United States Patent [19]
Labs

[11] Patent Number: 5,405,325
[45] Date of Patent: Apr. 11, 1995

[54] ACCESS GRAFT
[76] Inventor: Joseph D. Labs, 2515 No. 1 Longfellow Pl., Boston, Mass. 02114
[21] Appl. No.: 275,810
[22] Filed: Jul. 15, 1994

Related U.S. Application Data

[63] Continuation of Ser. No. 778,492, Oct. 17, 1991, abandoned.
[51] Int. Cl.⁶ .............................................. A61M 5/00
[52] U.S. Cl. .................................................. 604/93
[58] Field of Search ................. 604/93, 148, 153, 181, 604/183, 191, 201, 204, 212, 244, 284; 623/1, 12

[56] References Cited

U.S. PATENT DOCUMENTS

| | | | |
|---|---|---|---|
| 3,516,408 | 6/1970 | Montanti | 604/284 |
| 3,797,485 | 3/1974 | Urquhart | 604/93 |
| 3,826,257 | 7/1974 | Buselmeier . | |
| 3,998,222 | 12/1976 | Shihata . | |
| 4,014,328 | 3/1977 | Cluff et al. . | |
| 4,559,039 | 12/1985 | Ash et al. . | |
| 4,634,427 | 1/1987 | Hannula et al. . | |
| 4,710,167 | 12/1987 | Lazorthes . | |
| 4,710,174 | 12/1987 | Moden et al. . | |
| 4,738,657 | 4/1988 | Hancock et al. . | |
| 4,781,680 | 11/1988 | Redmond et al. . | |
| 4,840,172 | 6/1989 | Augustine et al. | 604/284 |
| 4,846,806 | 7/1989 | Wigness et al. . | |
| 5,006,115 | 4/1991 | McDonald . | |
| 5,026,344 | 6/1991 | Dijkstra et al. . | |
| 5,041,098 | 8/1991 | Loiterman et al. | 604/93 |
| 5,041,101 | 8/1991 | Seder et al. | 604/93 |
| 5,092,849 | 3/1992 | Sampson | 604/93 |
| 5,178,634 | 1/1993 | Martinez | 623/12 |

FOREIGN PATENT DOCUMENTS

| | | | |
|---|---|---|---|
| 2105197 | 3/1983 | United Kingdom | 623/12 |
| 9105522 | 5/1991 | WIPO | 623/12 |

OTHER PUBLICATIONS

May, J. W. & Rothkopf, M., "Salvage of a Failing Microvascular Free . . . ", Am. Soc. of Plastic & Reconstructive Surgeons, Jun. 1989.
Greenberg, B. M. et al., "Therapeutic Value of Intravenous Heparin . . . ", Am. Soc. of Plastic & Reconstructive Surgeons, Sep. 1988.
Trairatvorakul, P. et al., "Abdominal aortic aneurysms infected with . . . ", Journal of Vascular Surgery, vol. 12, No. 1, Jul. 1990.
Walsh, D. B. et al., "Intragraft drug infusion as an adjunct to balloon . . . ", J. Vascular Surgery, vol. 11, No. 6, Jun. 1990.
Wengrovitz, M., et al., "Cyclosporine inhibits the development of medial . . . ", J. Vascular Surgery, vol. 12, No. 1, Jul. 1990.
Baird, R. J., "Presidential address: Give Us the Tools . . . ", J. Vascular Surgery, vol. 11, No. 1, Jan. 1990.
Briggs, S. E. et al., "Distal Revasculariation & Microvascular Free Tissue . . . ", J. Vascular Surgery, vol. 2, No. 6, Nov. 1985.
Budd, J. S., et al., "The effect of varying fibronectin concentration . . . ", J. Vascular Surgery, vol. 12, No. 2, Aug. 1990.
Belkin, M. et al., "Observations on the use of thrombolytic agents . . . ", J. Vascular Surgery, vol. 11, No. 2, Feb. 1990.
Golden, M. A. et al., "Growth factor gene expression by intimal cells in . . . ", J. Vascular Surgery, vol. 11, No. 4, Apr. 1990.
Green, R. M. et al., "Comparison of infrainguinal graft surveillance . . . ", J. Vascular Surgery, vol. 11, No. 2, Feb. 1990.
Greisler, H. P. et al., "Effects of class I heparin binding growth factor . . . ", J. Vascular Surgery, vol. 11, No. 5, May 1990.

Primary Examiner—John D. Yasko
Assistant Examiner—Manuel Mendez
Attorney, Agent, or Firm—Cesari and McKenna

[57] ABSTRACT

An arterial access port which is grafted directly into the vascular system. The graft consists of a stem portion having at least one side branch extending from the stem for connection to an infusion port. The infusion port is in turn connected to a catheter or other similar device permitting the introduction of medication into the vascular system. The stem may take the form of a tubular section or an open surface for grafting into a side wall of a vascular channel. In use, medication or other material is first introduced through the access port, and then travels down the side branch to the venous system.

16 Claims, 2 Drawing Sheets

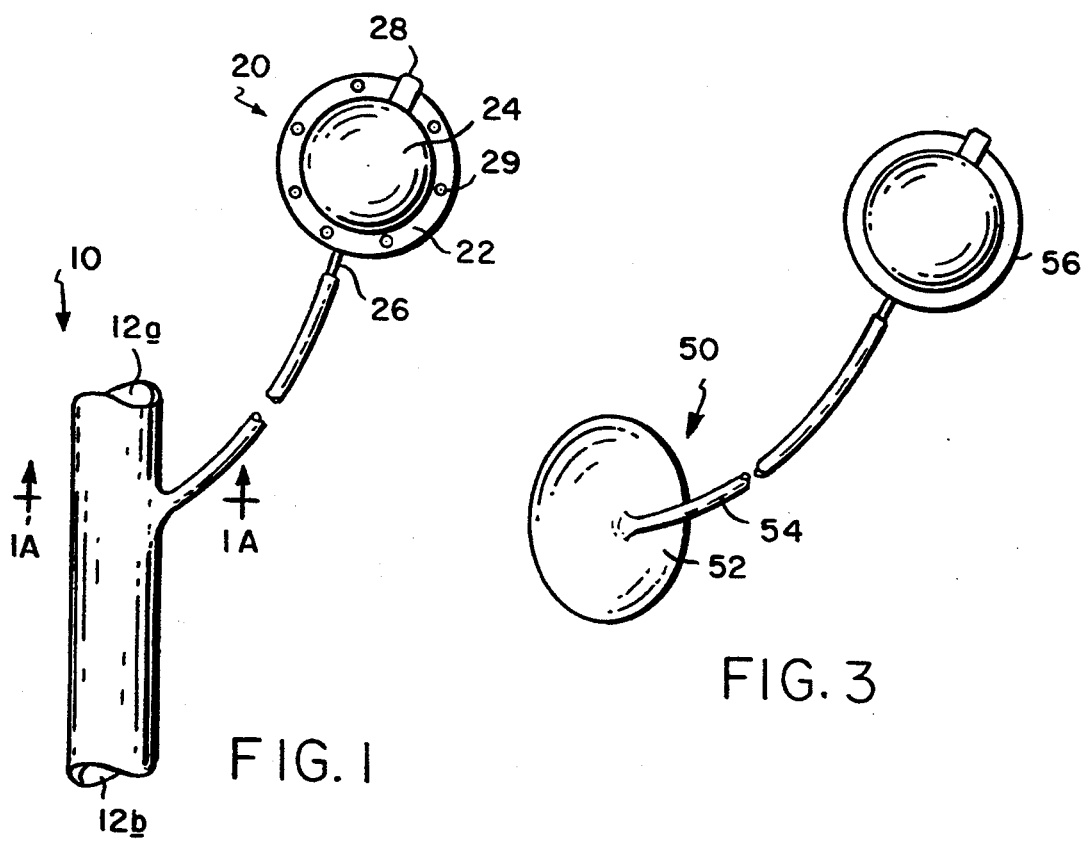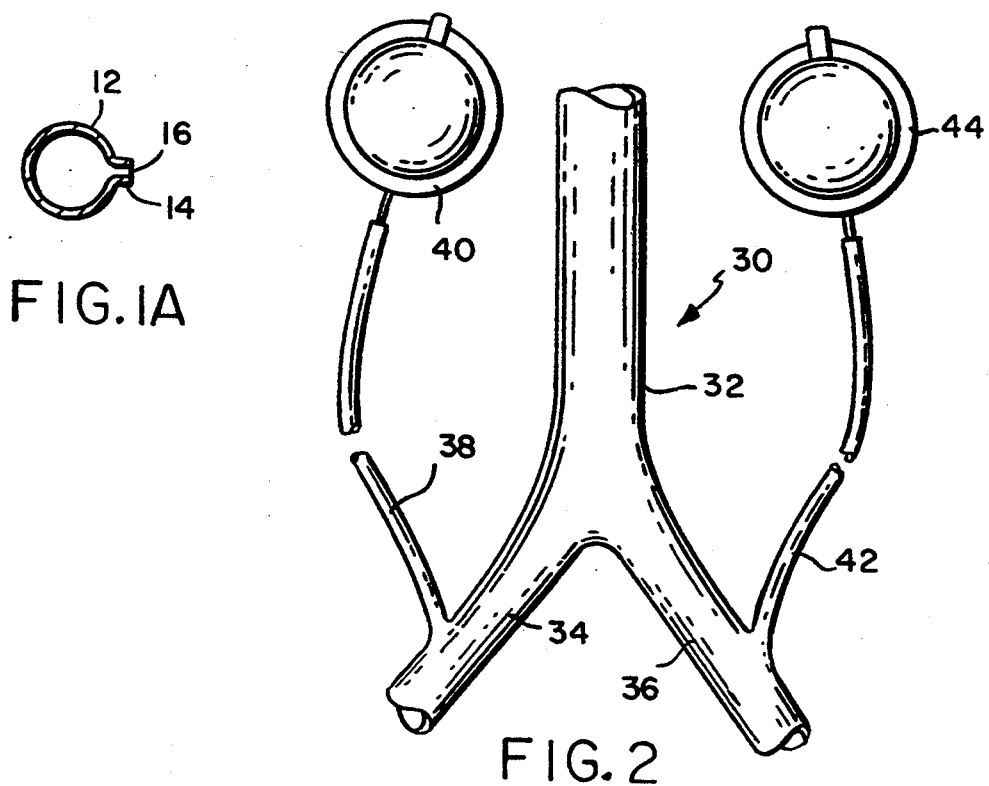

ically be in the leg, and the graft sutured into the

ACCESS GRAFT

This application is a continuation of application Ser. No. 07/778,492, filed Oct. 17, 1991, now abandoned.

BACKGROUND OF THE INVENTION

A. Field of the Invention

The invention relates to medical treatment devices and, more particularly, to devices for supplying medication or other materials to localized sites within the vascular system.

B. Prior Art

The diagnosis and treatment of defects in the vascular system presents a major challenge to the medical profession. The most effective methods for diagnosis and treatment of vascular disorders requires access to the vascular tree. Typically, this is accomplished by puncture of the vascular wall. Not only is this difficult in patients with diseases such as atherosclerosis, but complications such as bleeding and thromboembolisms increase the risk of such procedures. Thromboses are significant contributors to limb loss or deaths due to vascular failure, and yet themselves are frequent byproducts of vascular treatment.

Venous access is typically provided by means of catheters which puncture the vein. Access by this method has typically been short-term and limited to peripheral venous access because of complications such as thrombophlebitis. In-dwelling cathethers have been particularly susceptible to clot formation. In recent years, longer term central venous access has been provided by devices such as the Hickman catheter and the subcutaneous infusion port. These devices have markedly improved venous access, but have not been useful for arterial access because of such factors as substantially higher arterial pressure, among others. Indeed, the use of cathethers in arteries is recognized as especially dangerous.

DESCRIPTION OF THE INVENTION

A. Brief Summary of the Invention

In accordance with the present invention, I provide an access graft for providing long term access to the vascular system for such purposes as the localized delivery of medication and diagnostic or other materials into the vascular system, as well as for localized examination thereof. The graft is especially suited for use in the arterial system, where high pressures render many other types of delivery systems ineffective and long-term in-dwelling catheters are not acceptable.

The graft comprises a stem for grafting into the vascular system, and one or more tubular side branches extending from the stem for connection to an infusion port, a catheter, or other source of material for delivery to the vascular system or for providing access to the vascular system for diagnostic instruments. The stem may take the form of a tubular section, either single channel or branched, which is grafted in series with a vascular channel, or may take the form of an open surface grafted into a side wall of the vascular channel. As is the case with other grafts, the graft becomes a permanent part of the vascular system, unless otherwise removed.

For the delivery of medication, the side branch is connected to a subcutaneous infusion port. The port in turn may be connected to a catheter which extends through the skin and which terminates in a connector. Medication may be delivered to the infusion port (and thence to the graft site) either through the connector and its associated catheter or through injection through the skin directly into the infusion port.

B. Detailed Description of the Invention

The foregoing and other and further objects and features of the invention will more readily be understood from the following detailed description of the invention when taken in conjunction with the accompanying drawings in which:

FIG. 1 is a side elevational view of an access graft in accordance with the present invention, the graft having a single tubular branch to which a side branch connects, and showing an infusion port connected thereto;

FIG. 1A is a horizontal cross sectional view of the graft of FIG. 1 taken along the lines A—A of FIG. 1;

FIG. 2 is a side elevational view of another form of access graft in accordance with the invention, the graft having a plurality of branches therein;

FIG. 3 is a pictorial view of yet another form of access graft in accordance with the invention, the graft comprising an open surface or patch to which the side branch connects.

Figure 4:
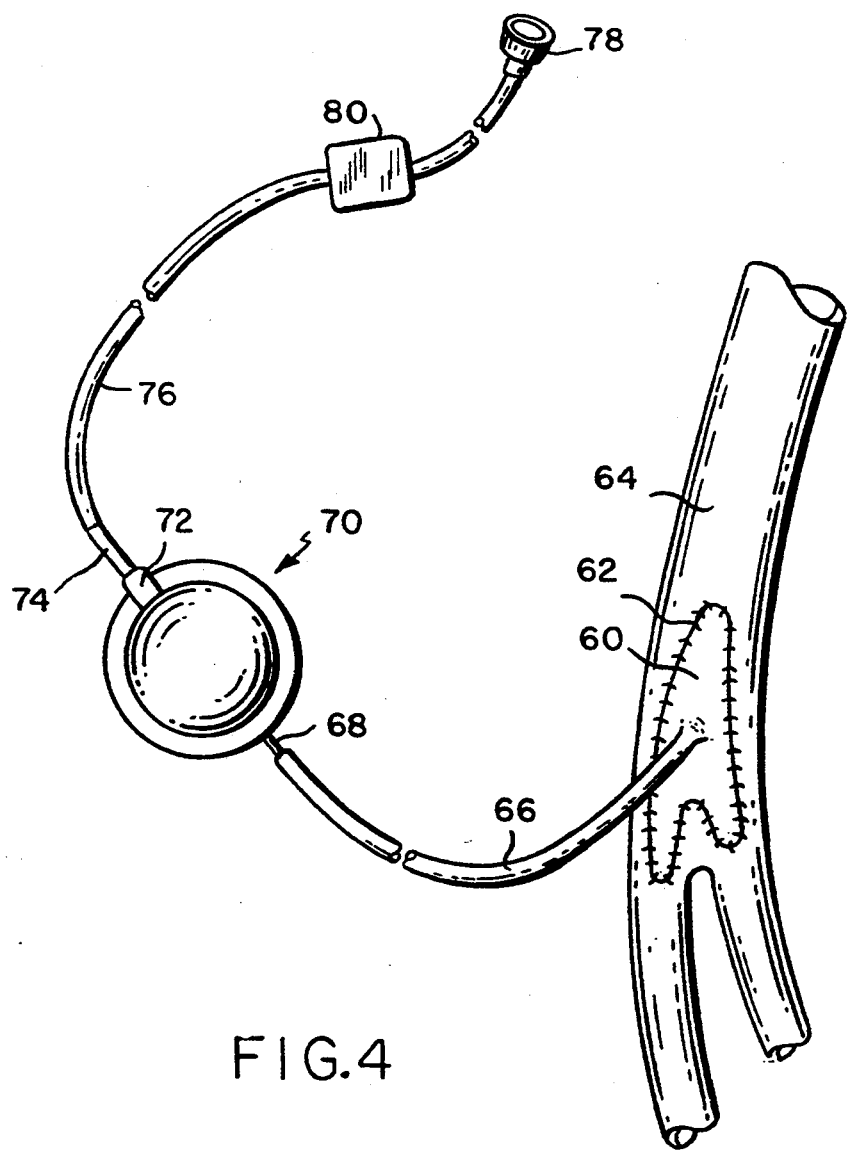
FIG. 4 is a pictorial view showing the access graft of FIG. 3 connected into the vascular system for the infusion of medication therein.

Referring now specifically to FIG. 1, an access graft 10 is formed from a tubular section 12 and a hollow side branch 14 extending therefrom and opening into the interior of the tubular section 10 through a port 16 (FIG. 1A). The graft and branch are formed from a suitable biocompatible material, such as PTFE TM (polytetrafluoroethylene) or the like. The branch is connected to an infusion port 20 of conventional type, known in the art; see, e.g., U.S. Pat. No. 4,781,680 issued Nov. 1, 1988 to Russell Redmond and Claude Vidal, for "Resealable Injection Site". For purposes of illustration herein, the port comprises a base 22, a hemispherical dome 24 sealed to the base and forming therewith a chamber for containing a fluid therein, an outlet port 26 connected to the side branch 14 for supplying fluid thereto, and an inlet port 28 for connection to an external source of fluid as shown in more detail in FIG. 4. Apertures 29 are provided around the base of the infusion port to facilitate anchoring the port within the body of a patient. The tubular branch snugly fits over the port 26 for fluid transfer therewith, and may be secured thereto with sealant or the like. The outlet port is occluded by a puncturable, resealable, skin which can be penetrated by a catheter or the like as described below in order to provide fluid access to the interior of the infusion port. For like reason, the surface 24 of the infusion port, is a puncturable, resealable skin of silicone rubber of the like.

In use, a suitable site for placement of the graft is surgically exposed and the upper and lower ends 12a and 12b, respectively, of the graft 10 are sutured or otherwise connected directly into the vascular tree of a patient, for example, into the arterial system. An infusion port 20 is then anchored to a suitable part of the patient's body by suturing or the like, and its outlet port 26 is connected to the side branch 14. The inlet port 28 of the infusion port 20 is then connected to a catheter which is brought out through the surface of the patient's skin for providing access to the infusion port and thus to the access graft. Alternatively, medication may be supplied to the infusion port through direct penetration of the port from the exterior of the patient's skin.

Turning now to FIG. 2, an alternative form of access graft 30 comprises a main tubular section 32 which diverges into subsidiary tubular sections 34, 36. Section 34 has a side branch 38 extending therefrom which connects to an infusion port 40; similarly, section 36 has a side branch 42 extending therefrom which connects to an infusion port 44. As was the case with the infusion port 18 or FIG. 1, the infusion ports 40, 44 are in turn connected to catheters which extend to the exterior of the patient's skin.

Another form of access graft is shown in FIG. 3. A stem 50 in the form of a patch 52 has a tubular side branch 54 extending therefrom. The side branch connects to an infusion port 56 in the manner described above in connection with FIGS. 1 and 2. The patch 52 is sutured or otherwise connected into the wall of an artery or vein for providing access thereto.

Turning now to FIG. 4, a complete graft access system is shown. For purposes of illustration, a patch 60 of the type shown in FIG. 3 is atached by means of sutures 62 into the wall of an artery 64. The patch carries a hollow side branch 66 which connects to an inlet port 68 of an infusion port 70. An outlet port 72 of the infusion port is penetrated by a needle 74 of a catheter 76 which terminates in a connector 78 to be positioned exteriorly of a patient's skin. A pad 80, of Teflon ™ or the like, is attached to the catheter 76 and is anchored just beneath the patient's skin to restrict movement of the catheter. Medication is applied through the connector 78, the catheter 76, the infusion port 70, the branch 66, and thus into the artery 64. Of course, in cases where access is desired for purposes other than the application of medication, for example, for purposes of providing access to probes or other instruments, the branch 66 may be disconnected from the port 68 of infusion port 70 and access by the instruments can be had directly through the branch 66.

The access graft of the present invention provides long-term access to the vascular system of a patient, and is particularly useful for providing arterial access, where high pressures and risk of clot have heretofore greatly limited and indeed largely precluded long-term access. The graft system provides the surgeon with a simple, convenient device for accessing the vascular system with minimal danger of clots or leakage. The grafts can be made in a variety of sizes, and with varying numbers and inclinations of branches so as to provide grafts that are specifically suited to a variety of graft sites and circumstances.

What is claimed is:

1. An arterial access graft for delivering medication to an artery of an animal body, comprising:
a stem means for grafting into said artery;
means forming a hollow side branch on said stem means, for delivering said medication to the interior thereof, said side branch terminating at a first end in a first port opening into the interior of said stem means and terminating at a second end in a second port for connection to a source of the medication for delivery to said artery; and
subcutaneous infusion port means, connected to said second port, for delivery of medication thereto.

2. An arterial access graft according to claim 1 in which said stem means comprises a tubular section.

3. An arterial access graft according to claim 1 in which said stem means comprises a tubular section having a plurality of tubular channels diverging therefrom, and in which at least one of said channels has a side branch extending therefrom.

4. An arterial access graft according to claim 1 in which said stem means comprises a tubular section having a plurality of tubular channels diverging therefrom, and in which a plurality of said channels have side branches extending therefrom.

5. An arterial access graft according to claim 1 in which said stem means comprises a tubular section having a plurality of tubular channels diverging therefrom, and in which each of said channels haa a side branch extending therefrom.

6. An arterial access graft according to claim 1 in which said stem means comprises a patch for grafting into the wall of said artery.

7. An access graft for delivering medication to the vascular system of an animal body, comprising
stem means for grafting into a conduit of said vascular system;
means forming a hollow side branch on said stem means, for delivering said material to the interior thereof, said side branch terminating at a first end in a first port opening into the interior of said stem means and terminating at a second end in a second port for connection to a source of medication for delivery to said conduit; and
subcutaneous infusion port means, connected to said second port, for delivery of medication thereto.

8. An access graft according to claim 7 in which said stem means comprises a tubular section.

9. An access graft according to claim 8 in which said stem means comprises a tubular section having a plurality of tubular channels diverging therefrom, and in which at least one said channels has a side branch extending therefrom.

10. An access graft according to claim 7 in which said stem means comprises an open surface for grafting into the wall of said conduit.

11. An access graft according to claim 1 in which said subcutaneous infusion port means includes a puncturable, resealable surface for penetration by a medication delivery vehicle.

12. An access port according to claim 7 in which said subcutaneous infusion port means includes a puncturable, resealable surface for penetration by a medication delivery vehicle.

13. An access port according to claim 12 in which said subcutaneous infusion port means includes first and second puncturable, resealable surfaces for penetration by multiple medication delivery vehicles.

14. An access port according to claim 1 additionally comprising:
a catheter connected to said subcutaneous infusion port means.

15. An access port according to claim 7 additionally comprising:
a catheter connected to said subcutaneous infusion port means.

16. An access graft connected to deliver medication to the vascular system of an animal body, comprising:
a stem grafted into a conduit of said vascular system;
a hollow side branch on said stem, said side branch terminating at a first end in a first port opening into the interior of said stem and terminating at a second end in a second port; and
a subcutaneous infusion port, connected to said second port.

* * * * *